(12) United States Patent
Oh et al.

(10) Patent No.: US 7,413,707 B2
(45) Date of Patent: Aug. 19, 2008

(54) MICROCHIP ASSEMBLY

(75) Inventors: Kwang-wook Oh, Hwaseong-si (KR);
Yu-jin Seo, Daejeon-si (KR)

(73) Assignee: Samsung Electronics Co., Ltd. (KR)

( * ) Notice: Subject to any disclaimer, the term of this patent is extended or adjusted under 35 U.S.C. 154(b) by 283 days.

(21) Appl. No.: 11/430,741

(22) Filed: May 9, 2006

(65) Prior Publication Data

US 2006/0286582 A1  Dec. 21, 2006

(30) Foreign Application Priority Data

Jun. 17, 2005  (KR) .................. 10-2005-0052579

(51) Int. Cl.
*B01D 59/44* (2006.01)

(52) U.S. Cl. .................. 422/50; 250/288; 422/49; 422/58; 422/61; 422/63; 422/62; 422/68.1; 422/81

(58) Field of Classification Search .......... 250/281–300
See application file for complete search history.

(56) References Cited

U.S. PATENT DOCUMENTS

| 5,705,813 | A  | * | 1/1998 | Apffel et al. | 250/288 |
| 6,596,988 | B2 | * | 7/2003 | Corso et al. | 250/288 |
| 6,956,207 | B2 | * | 10/2005 | Corso et al. | 250/288 |
| 2002/0000516 | A1 | * | 1/2002 | Schultz et al. | 250/288 |
| 2007/0114385 | A1 | * | 5/2007 | Sarrut | 250/288 |

* cited by examiner

*Primary Examiner*—Jack I. Berman
*Assistant Examiner*—Andrew Smyth
(74) *Attorney, Agent, or Firm*—Cantor Colburn LLP (57) ABSTRACT

Provided is a microchip assembly including a base holder, a microchip installed on the base holder and having at least one input hole into which a reaction sample is input and at least one microchamber accommodating the input reaction sample, a flipper rotatably installed at the outside of the microchip on the base holder and opening and closing the input hole of the microchip while flipping up in a vertically erected state or flipping down in a horizontal state, and slider installed at the outside of the flipper on the base holder to be capable of sliding and supporting the flipper in the erected state and flipping down the flipper while moving inside.

21 Claims, 10 Drawing Sheets

MICROCHIP ASSEMBLY

CROSS-REFERENCE TO RELATED PATENT APPLICATIONS

This application claims the benefit of Korean Patent Application No. 10-2005-0052579, filed on Jun. 17, 2005, in the Korean Intellectual Property Office, the disclosure of which is incorporated herein in its entirety by reference.

BACKGROUND OF THE INVENTION

1. Field of the Invention

The present invention relates to a microchip assembly, and more particularly, to a microchip assembly which accommodates a mixed sample subject to reaction and seals the mixed sample to provide a reaction environment.

2. Description of the Related Art

Microchambers are needed for study and analysis of reaction of a very small material in the fields of biotechnology, genetic engineering and diagnostic medicine. Among them, polymerase chain reaction (PCR) is to amplify a desired gene in a particular space by characteristically and repeatedly synthesizing a particular gene. That is, a great amount of the same replicated gene is obtained using a very small amount of the gene. The synthesis of gene is performed by injecting a sample mixed with a gene subject to the PCR and a reagent needed for the PCR such as a polymerase, a single base, or a polymerization reagent, in a microchamber, and repeating heating to temperatures needed for reaction and cooling.

Conventionally, the sample is directly injected into the microchamber using a pipette. That is, a reaction sample is manually and directly injected into the microchamber and heated to an about 100° C. The microchamber is sealed with an optical tape to prevent evaporation of the material accommodated in the microchamber during the above heat circulation reaction. However, the sample injection job needs a careful manipulation so that the sample may leak according to a degree of expertness. In particular, a multi-chamber method is used which can process a plurality of samples at the same time. When different samples are accommodated in the multi-chamber, the samples may be mixed during injection so that reliability of a reaction result can be deteriorated.

BRIEF SUMMARY OF THE INVENTION

To solve the above and/or other problems, the present invention provides a microchip assembly which can facilitate sealing of a microchamber.

The present invention provides a microchip assembly in which a reaction sample can be accurately injected in a microchamber without leaking of the sample or confusion.

According to an aspect of the present invention, a microchip assembly comprises a base holder, a microchip installed on the base holder and having at least one input hole into which a reaction sample is input and at least one microchamber accommodating the input reaction sample, a flipper rotatably installed at the outside of the microchip on the base holder and opening and closing the input hole of the microchip while flipping up in a vertically erected state or flipping down in a horizontal state, and slider installed at the outside of the flipper on the base holder to be capable of sliding and supporting the flipper in the erected state and flipping down the flipper while moving inside.

The flipper is arranged in a pair to face each other with respect to the microchip. The slider is arranged in a pair at the outside of the flipper.

An accommodation hole that provides an accommodation space for the microchip is formed in the base holder and a support portion formed along the edge of the accommodation hole to be stepped downward and preventing escape of the microchip.

A pair of guide members between which the flipper and the slider are inserted and fixed are formed at the outside of the microchip on the base holder. A guide piece protruding in a direction is formed on the guide member and a guide groove having a shape matching the shape of the guide piece is formed at the slider.

A hinge shaft protrudes from both sides of the flipper and a through hole is formed in the guide member into which each hinge shaft is inserted and hinge coupled.

An elastic press member is formed at a bottom portion of the flipper covering the microchip. A cavity is formed at the bottom portion of the flipper and the elastic press member is fixedly inserted in the cavity. The elastic press member protrudes from a bottom surface of the flipper to form a step. The elastic press member seals the input hole of the microchip in an elastically compressed state so that a bottom surface of the elastic press member forms the same plane with the bottom surface of the flipper.

The elastic press member is formed of PDMS or silicon rubber as a main material.

A hook step is formed on a surface of the flipper opposite to the microchip and the flipper is flipped up by a holding unit placed on the hook step. A metal pad is formed on a surface of the flipper opposite to the microchip and the flipper pivots into a flip-up state by a permanent magnet which acts a magnetic attraction to the metal pad.

A cap housing is accommodated on the base holder and at least one injection hole through which the reaction sample is injected toward the microchip thereunder is formed in the cap housing. The injection hole has a shape matching the injection tool.

The injection hole is shaped into a funnel and the injection tool inserted into the injection hole is a pipette. A female teeth portion is formed at the injection hole and a male teeth portion matching the female teeth portion is formed at the injection tool that is inserted in the injection hole.

A lower end surface of the cap housing forms a horizontal surface and contacts the base holder, a protruding press piece protrudes downward than the lower surface of the cap housing from a portion of the cap housing facing the microchip, and the protruding press piece fixedly presses the microchip. An indication mark to identify the injection holes formed in multiple numbers is formed on the cap housing. The cap housing is formed of an optically transparent material.

BRIEF DESCRIPTION OF THE DRAWINGS

The above and other features and advantages of the present invention will become more apparent by describing in detail preferred embodiments thereof with reference to the attached drawings in which.

DETAILED DESCRIPTION OF THE INVENTION

Figure 1:
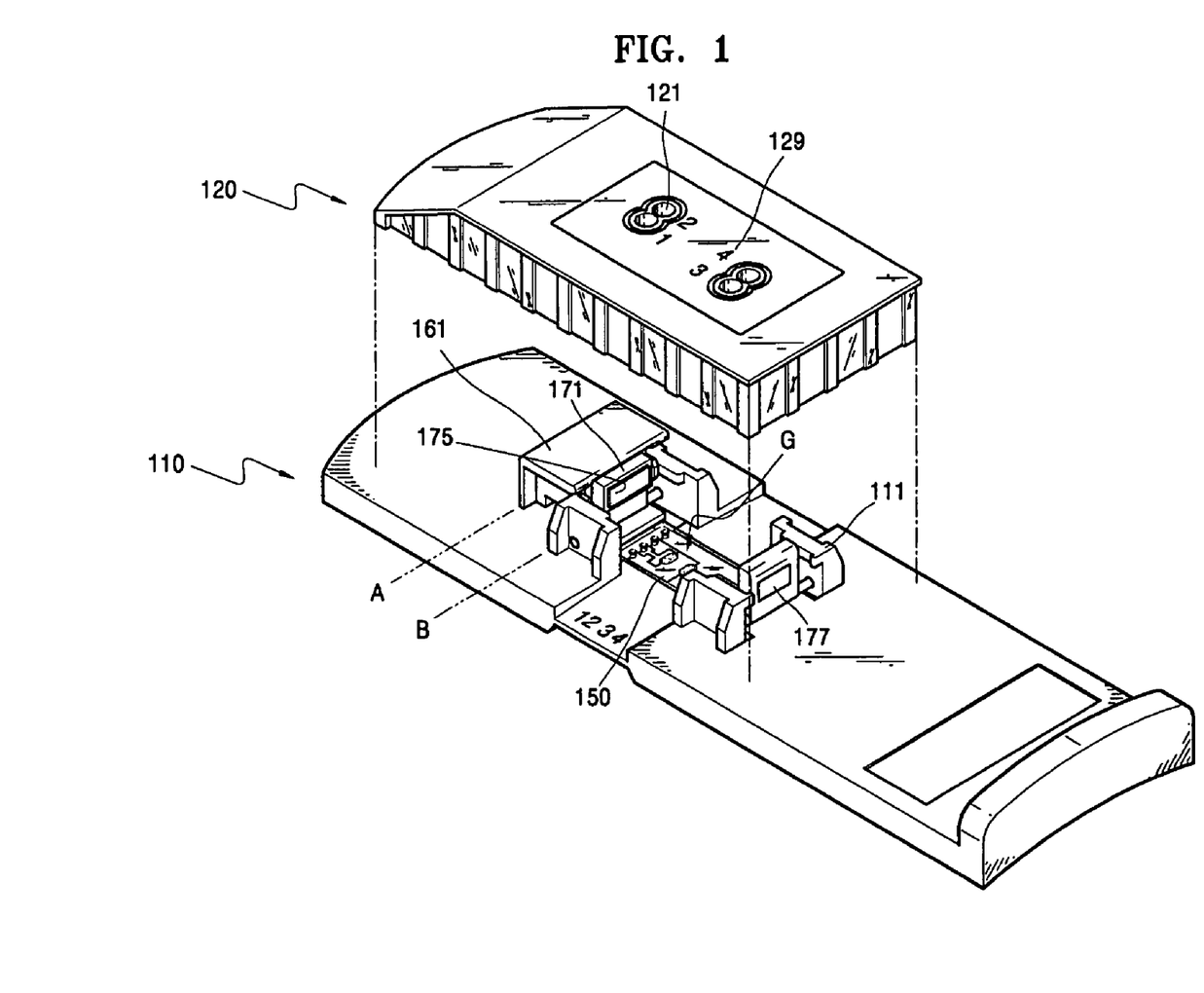
FIG. 1 is an exploded perspective view of a microchip assembly according to an embodiment of the present invention.
Figure 2:
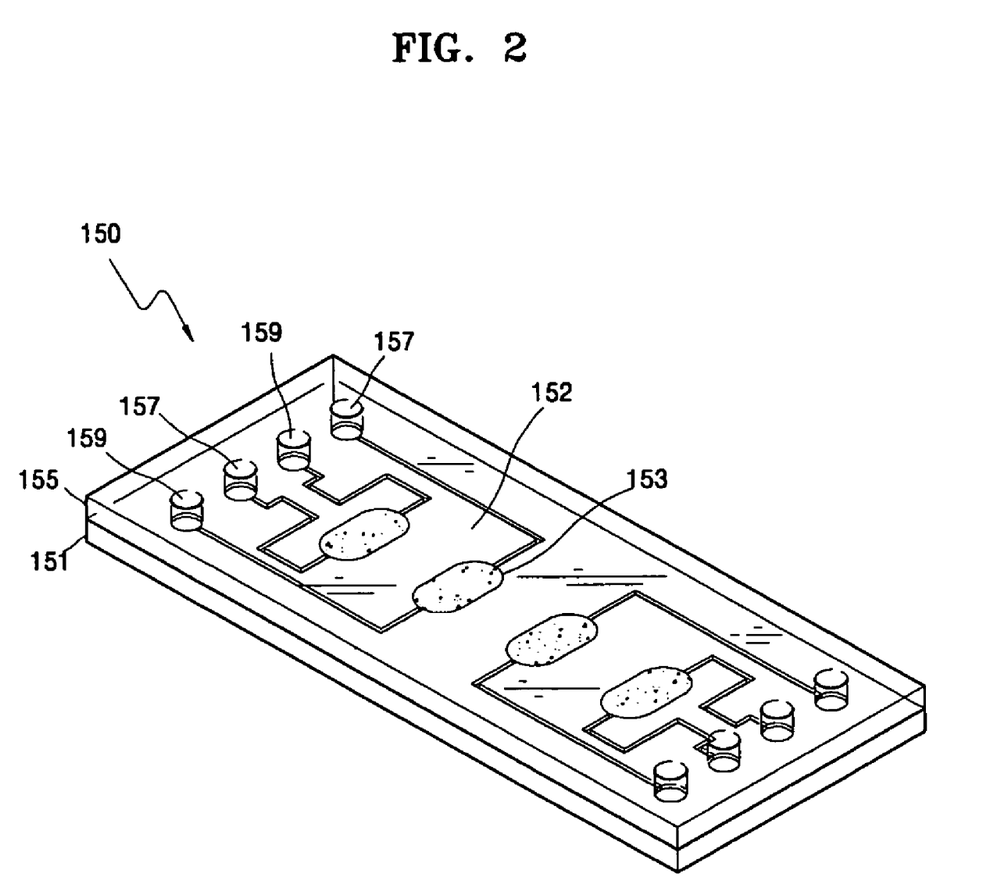
FIG. 2 is a perspective view of the microchip shown in FIG. 1.

FIG. 1 is an exploded perspective view of a microchip assembly according to an embodiment of the present invention. FIG. 2 is a perspective view of the microchip shown in FIG. 1. Referring to FIG. 1, a microchip assembly according to an embodiment of the present invention includes a microchip 150 into which a reaction sample is injected and a base holder 110 for accommodating the microchip 150. A cap housing 120 is mounted on the base holder 110 where the microchip 150 is installed.

Referring to FIG. 2, the microchip 150 includes an accommodation member 151 and a cover member 155 which are bonded to face each other. The cover member 155 at the upper side of the microchip 150 prevents evaporation of the reaction sample accommodated in the microchip 150 and entrance of the foreign material. A pair of an input hole 157 and a vent hole 159 connected to a microchamber 153 through a flow lane 152 are formed in the cover member 155. In detail, the input hole 157 and the vent hole 159 form pairs inside and outside are connected to different microchamber 153. The reaction sample that is a mixture of a gene sample, enzyme such as polymerase needed for PCR, and other necessary reagents is supplied through the input hole 157. As the reaction sample is input to the microchamber 153, impurity gas filling the microchamber 153 is exhausted through the vent hole 159. The cover member 155 can be formed of, for example, a transparent glass material.

The microchamber 153 and the flow lane 152 which are etched to have predetermined shapes are formed in the accommodation member 151 which faces and is coupled to a lower side of the cover member 155. The sample input to the inside of the microchip 150 is guide by the flow lane 152 to move to the microchamber 153. The flow lane 152 has a narrow width and moves the sample toward the microchamber 153 using a capillary phenomenon. The impurity gas filling the microchamber 153 is guided by the flow lane 152 connected to the microchamber 153 to move toward the vent hole 159 and then exhausted to the outside.

The accommodation member 151 can be formed of a material exhibiting a superior thermal conductivity, for example, silicon. When the microchip accommodating the reaction sample is installed on a thermal cycler which provides a thermal circulation reaction, heat energy is provided to the reaction sample from a heating plate (not shown) through the lower side of the accommodation member 151. Thus, the heat circulation reaction is initiated.

As shown in FIG. 1, the microchip 150 configured as above is installed on the base holder 110. In detail, an accommodation hole G having a rectangular shape is formed at the center of the base holder 110 and a support portion 115 (please refer to FIG. 3) stepped downward is formed along the edge of the accommodation hole G. The microchip 150 is supported by the support portion 115 so as to be prevented from escaping from the base holder 110. The bottom surface of the microchip 150 that is installed at the base holder 110 is exposed and the exposed bottom surface of the microchip 150 closely contacts the heating plate so that the microchip 150 is heated according to a predetermined thermal cycle.

A plurality of guide members 111 are formed on the base holder 110 adjacent to the accommodation hole G. In detail, two pairs of the guide members 111 are symmetrically formed at the left and right sides to face each other. A slider 161 is supported between each pair of the guide members 111 capable of sliding and the forward and backward movement of the slider 161 is guided by the guide members 111. Although FIG. 1 illustrates that the slider 161 is inserted between the guide member 111 at the left side only for the convenience of explanation, another same slider is inserted between the guide members 111 at the right side to make a left and right symmetry.

Figure 3:
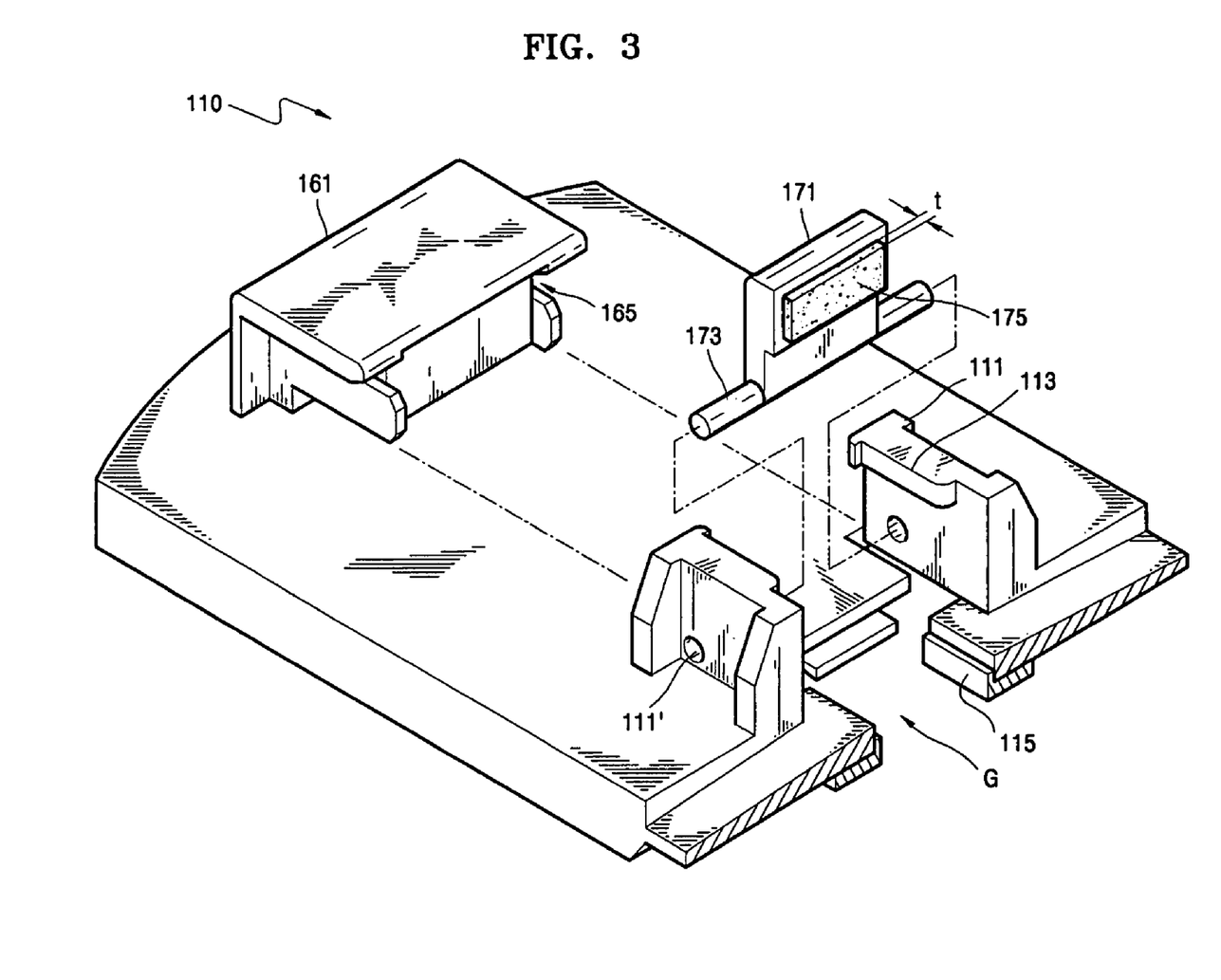
FIG. 3 is an enlarged perspective view of a portion of the microchip assembly of FIG. 1.

FIG. 3 is an enlarged perspective view of a portion of the microchip assembly of FIG. 1. Referring to FIG. 3, a guide groove 165 is formed in a direction at both sides of the slider 161. The slider 161 is coupled between the guide member 111 such that the guide groove 165 fits to a guide piece 113 protruding parallel to the guide members 111.

A flipper 171 is hinged between each pair of the guide members 111 capable of rotating under the slider 161. In detail, as a hinge shaft 173 of the flipper 171 is inserted into a through hole 111' formed in each of the guide member 111, the flipper 171 is supported and capable of rotating around the hinge shaft 173. The flipper 171 opens or closes the input hole 157 of the microchip 150 while pivoting around the hinge shaft 173 inserted into the guide members 111.

An elastic press member 175 is arranged on a surface of the flipper 171 facing the base holder 110. The elastic press member 175 is fixed to the flipper 171 by being forcibly inserted into a cavity (not shown) formed in a predetermined area on a bottom surface of the flipper 171. The elastic press member 175 protrudes from the bottom surface of the flipper 171 to have a predetermined step "t". When the flipper 171 pivots toward the base holder 110 and flips down to close the input hole 157 of the microchamber 150, the elastic press member 175 is compressed as much as the step t. The compression of the elastic press member 175 generates an elastic force so that the microchip 150 is pressed and closed. Thus, even when the reaction sample accommodated in the microchip 150 undergoes a thermal cycle and heated to a predetermined temperature, a sealing state can be maintained against steam pressure generated due to heating. The elastic press member 175 has a buffering feature or elasticity and is formed of, for example, PDMS or silicon rubber. Other than the elastic press member 175, the base holder 110, the slider 161, and the flipper 171 can be formed of a polymer resin material such as polycarbonate or polyethylene.

Figure 4:
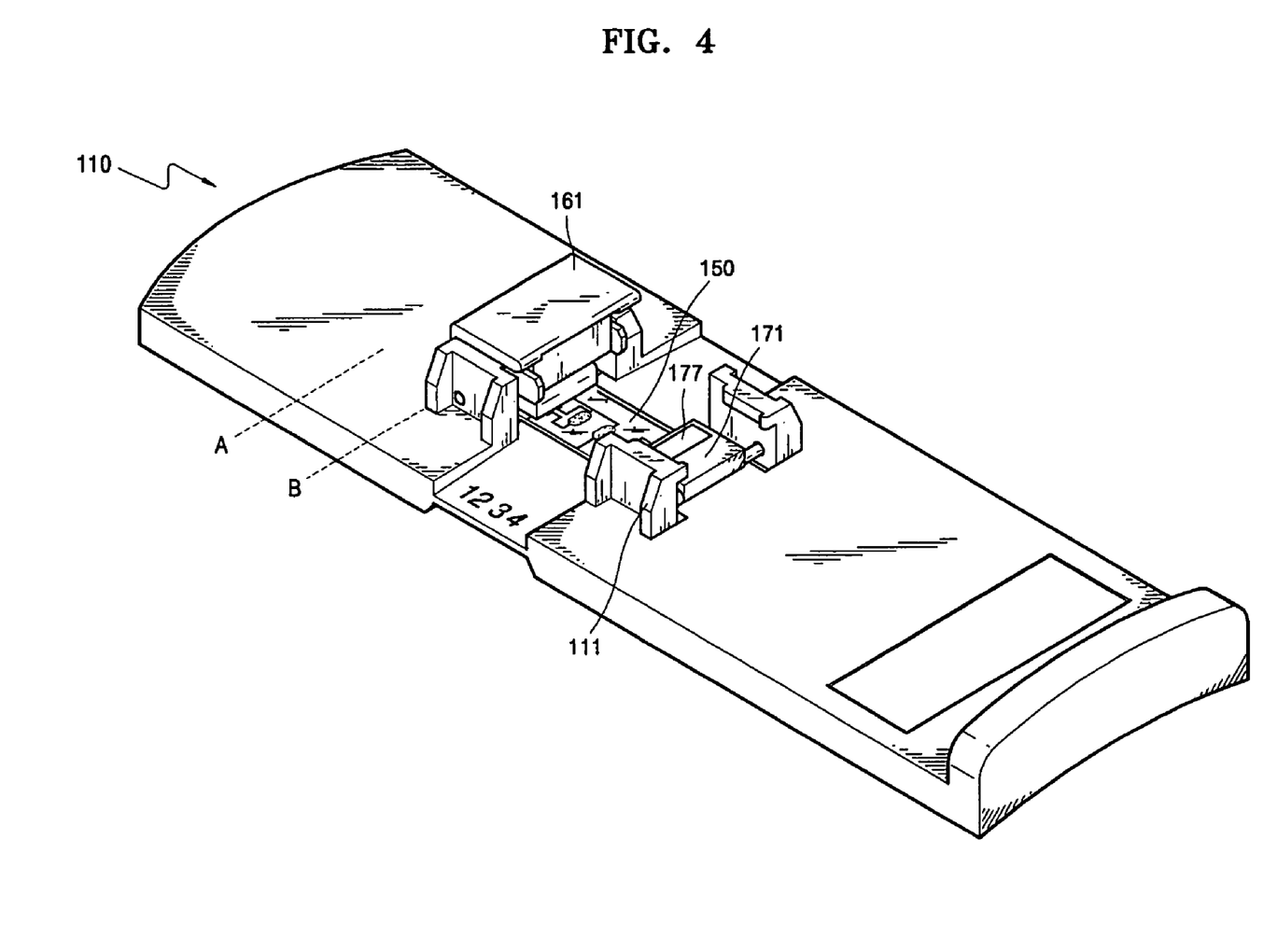
FIG. 4 is a perspective view of a portion of the microchip assembly of FIG. 1, showing a flip-down state.

The flip operation of the flipper 171 is described below in detail. As shown in FIG. 1, the flipper 171 in a flip-up state is supported to be erected by the slider 161 arranged outside. In the flip-up state, the microchip 150 installed on the base holder 110 is in an open state so that the reaction sample can be injected into the microchip 150 through the input hole 157. When the reaction sample is completely injected, as shown in FIG. 4, the slider 161 is manually moved from a position A to a position B at the inner side. The movement of the slider 161 flips down the flipper 171 to cover the microchip 150 installed on the base holder 110. That is, the flipper 171 in the erected state by the slider 161, as shown in FIG. 1, is pushed by the slider 161 that moves to the inner side and pivots toward the base holder 110 around the hinge shaft 173. Thus, the flipper 171 maintains a horizontal posture by being accommodated on the microchip 150, as shown in FIG. 4.

After the reaction is completed, the sample accommodated in the microchip 150 is removed. To this end, the slider 161 is moved from the position B to the position A and the flipper 171 covering the microchip 150 is rotated upward. This flip-up motion is performed manually and a flip-up unit can be provided at the flipper 171 to easily hold and pull up the flipper 171. The flip-up unit may be a hook step formed at an appropriate portion of the flipper 171, for example, on a surface opposite to the base holder 110 of the flipper 171. The flipper 171 can be flipped up to an open position by holding the hook step and pulling up using a holding unit, for example, tweezers.

Alternatively, a flip-up unit 177 shown in FIG. 4 is a metal pad formed on a surface opposite to the base holder 110 of the flipper 171. As a rod member (not shown) having a permanent magnet formed at a tip end thereof contacts the metal pad and is pulled upward, the flipper 171 can be easily rotated upward and opened.

Figure 5:
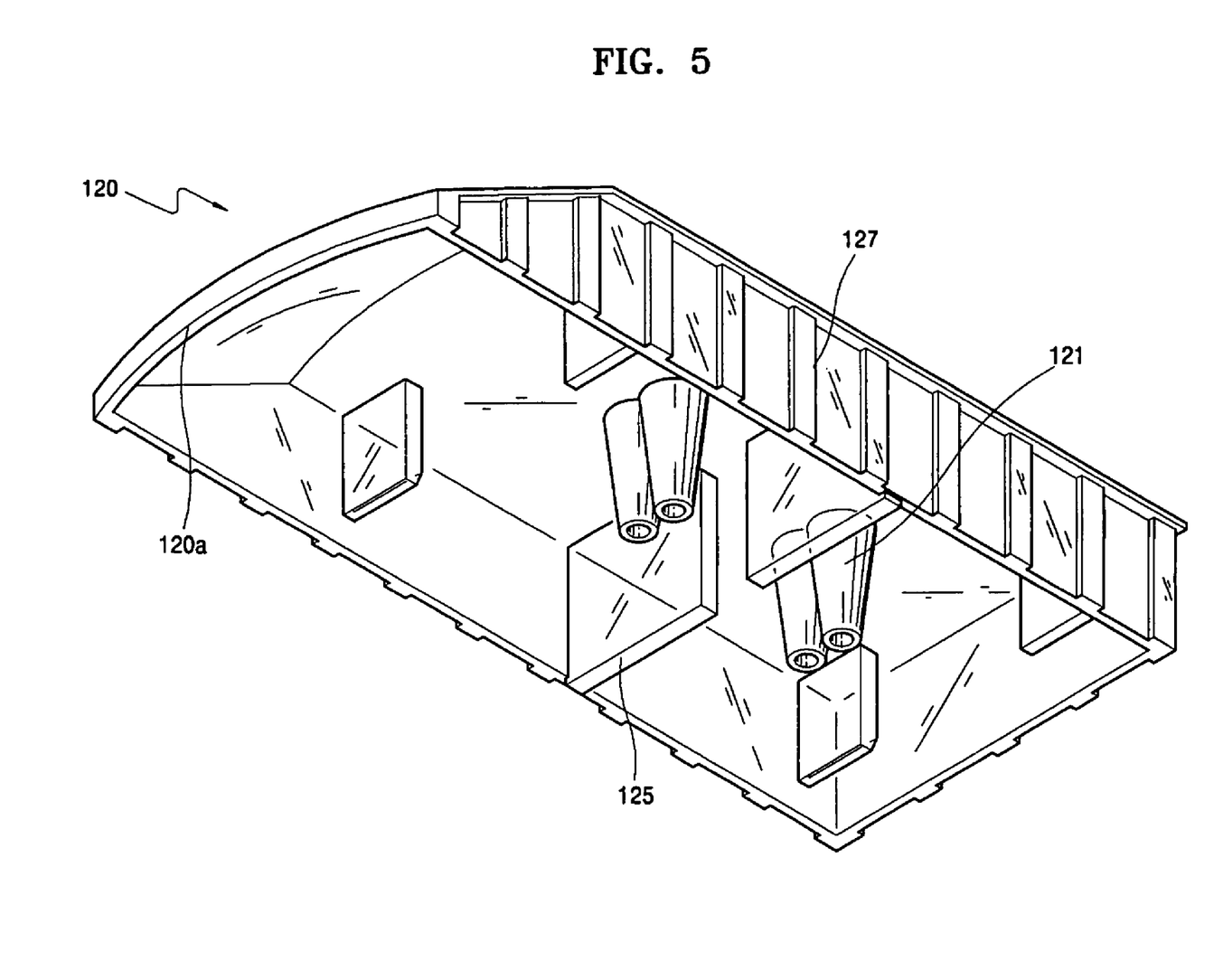
FIG. 5 is a perspective view of a cap housing shown in FIG. 1, viewed from the lower side.

A space portion is provided in the base holder 110 so that the cap housing 120 covering the elements on the base holder 110 is accommodated in the space portion. FIG. 5 shows an example of the cap housing 120, viewed from the lower side. Referring to FIG. 5, the cap housing 120 is formed of an optically transparent material so that the interior structure of the base holder 110 can be seen when the cap housing 120 is installed. The optically transparent material can be, for example, polyethylene terephthalate (PET), PC, or PMMA.

At least one injection hole 121 through which the reaction sample is input is formed in the cap housing 120. For example, four injection holes 121 can be formed in the cap housing 120. However, the number of the injection holes 121 can be increased or decreased corresponding to the number of the microchamber 153 formed in the microchip 150. Each of the injection holes 121 is connected to the microchip 150 thereunder, in detail, the input hole 157 of the microchip 150.

An injection tool (not shown) for transferring the reaction sample to the microchip 150 is inserted into the injection hole 121. The injection hole 121 holds the injection tool at a right position so that the reaction sample is injection into a right position and prevented from leaking. The injection hole 121 is formed to correspond to the injection tool inserted therein. For example, when a typical pipette is used as the injection tool, the injection hole 121 can be formed to have a funnel shape. In addition to the pipette, a silicon tube, a capillary tube, or a syringe may be used as the injection tool. Accordingly, the injection hole 121 of the cap housing 120 is formed to match the shape of each injection tool. For example, when a male teeth portion is formed at the injection tool and a female teeth portion matching the male teeth portion is formed at the injection hole 121 of the housing 120, accurate fitting therebetween is possible so that the leakage of the reaction sample can be prevented.

An indication mark 129 for identifying the injection hole 121 (please refer to FIG. 1) can be formed on the upper surface of the cap housing 120. When different reaction sample is input through the injection hole 121, the reaction sample can be accurately input through the injection hole 121 without confusion with the assistance of the indication mark 129.

A lower end surface 120a of the cap housing 120 is accommodated on the upper surface of the base holder 110 to face each other. A protruding press piece 125 extends from the approximately middle portion of each of longer side portions 127 in the opposed directions. The protruding press piece 125 forms a step downward with respect to the lower end surface 120a. Accordingly, the protruding press piece 125 presses the microchip 150 installed on the base holder 110 with a predetermined pressure so that the microchip 150 is closely fixed between the protruding press piece 125 at the upper side and the support portion 115 at the lower side. As a result, when the cap housing 120 is accommodated on the base holder 110, the protruding press piece 125 at the middle portion presses the microchip 150 and the lower end surface 120a of the cap housing 120 contacts the upper surface of the base holder 110. A protective tape 131 (please refer to FIG. 6A) is attached to the upper surface of the cap housing 120 so that the injection hole 121 is prevented from being connected to the outside. This is because, if foreign material such as dust is input to the inside through the injection hole 121, the purity of a reaction sample and the reliability of a reaction result are deteriorated.

Figure 6A:
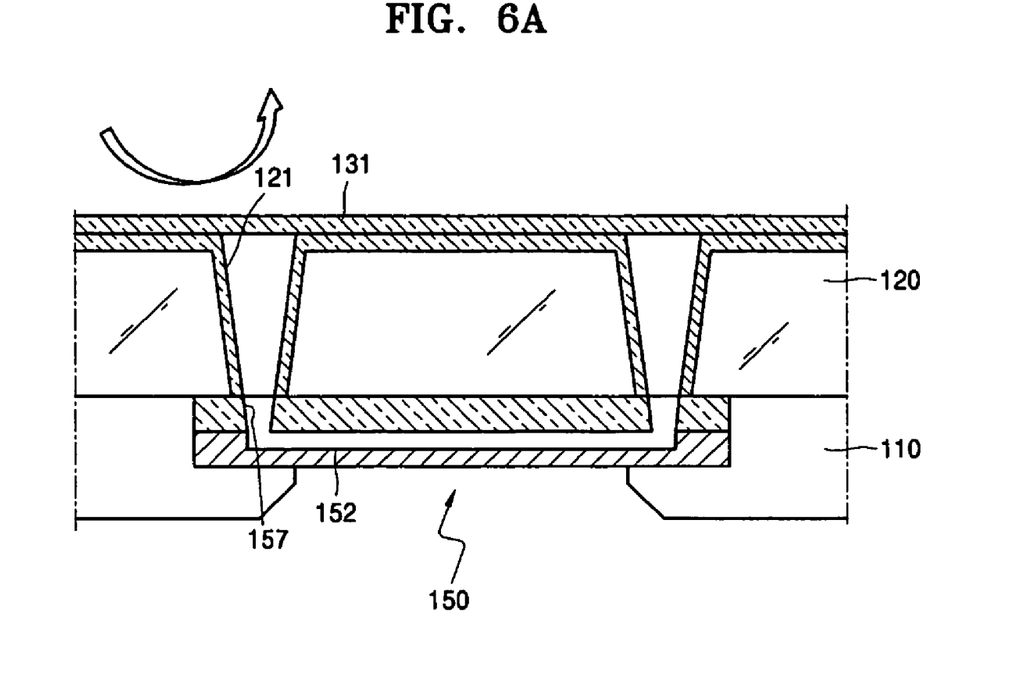
FIGS. 6A through 6F are cross-sectional views of a portion of the microchip assembly to explain the operation state.
Figure 6B:
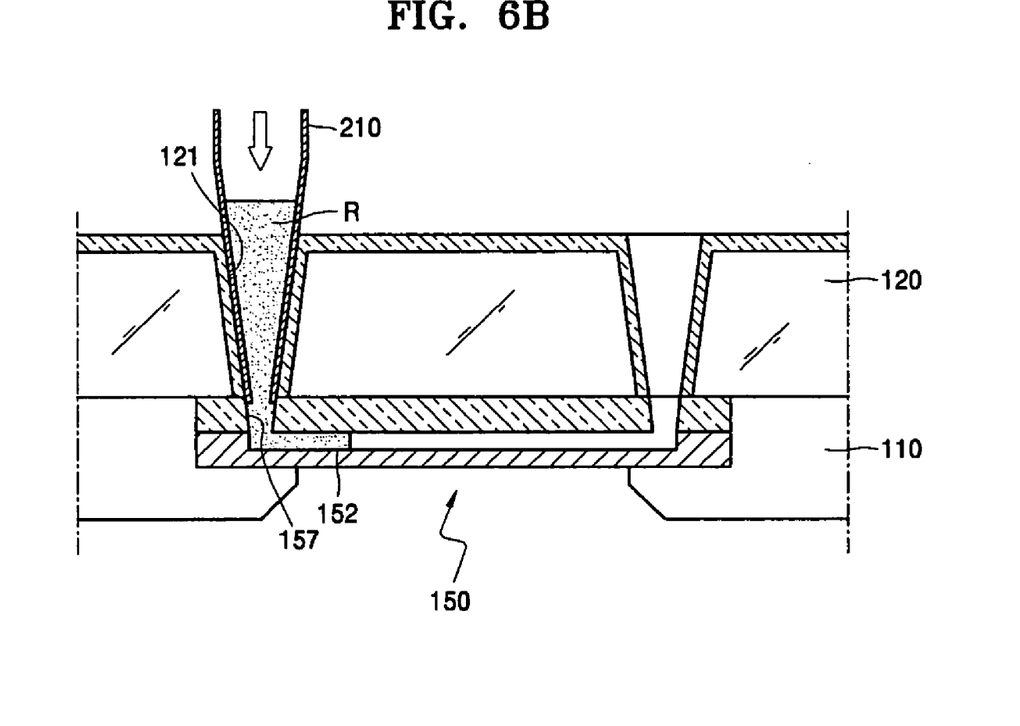

FIGS. 6A through 6F show the sequential operation of the microchip assembly. As shown in FIG. 6A, the microchip assembly is provided with the protective tape 131 attached to the upper surface thereof. The protective tape 131 is removed by a user for use so that the injection hole 121 of the cap housing 120 is open. Next, as shown in FIG. 6B, a pipette 210 as the injection tool is inserted into the injection hole 121 that is open and a reaction sample R is injected into the inside of the microchip 150 through the input hole 157. The reaction sample R is moved toward the microchamber by being guided by the flow lane 152. As the reaction sample R moves along the flow lane 152, impurity gas existing in the microchamber is moved to the vent hole 159 by being guided by the flow lane 152 connected to the microchamber and exhausted to the outside of the microchip assembly.

Figure 6C:
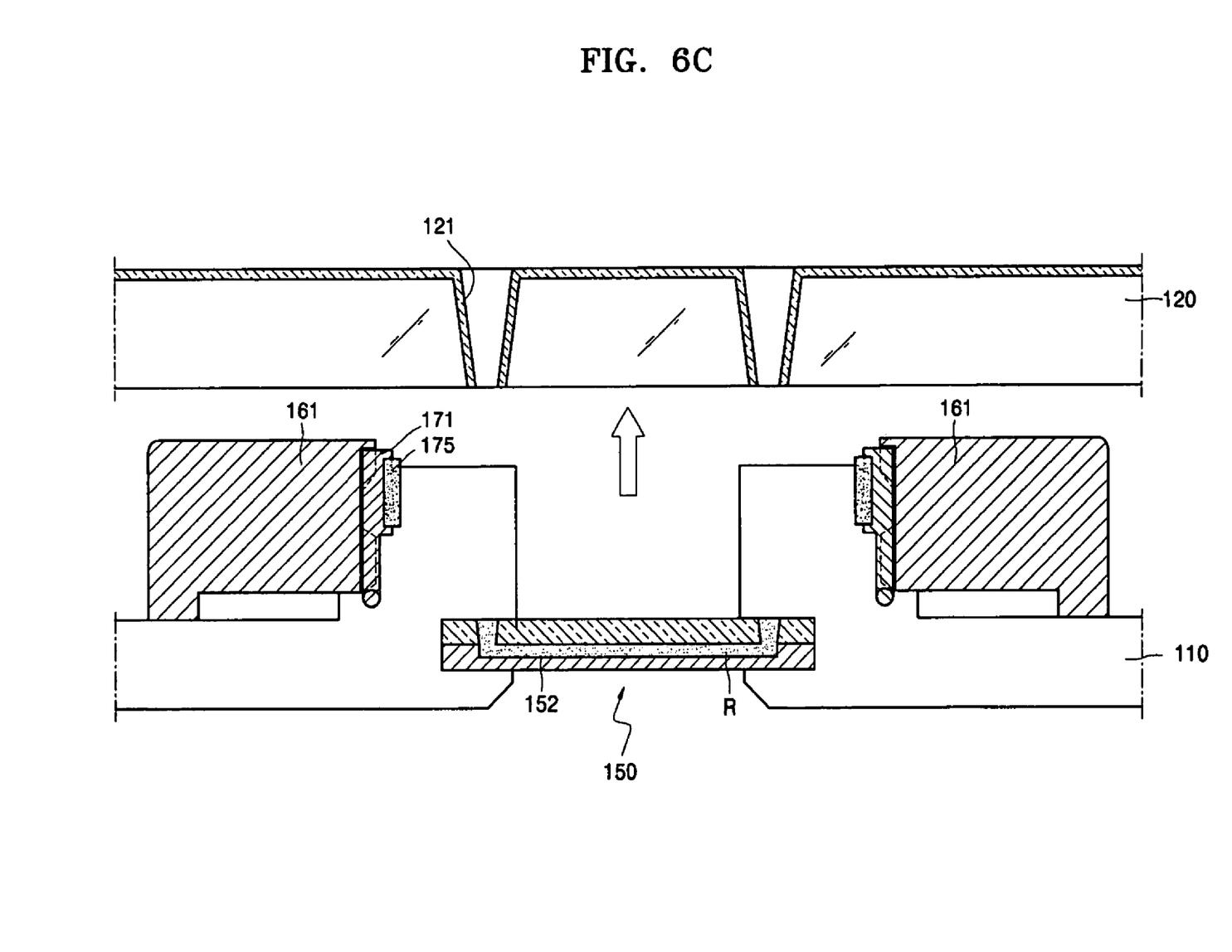
Figure 6D:
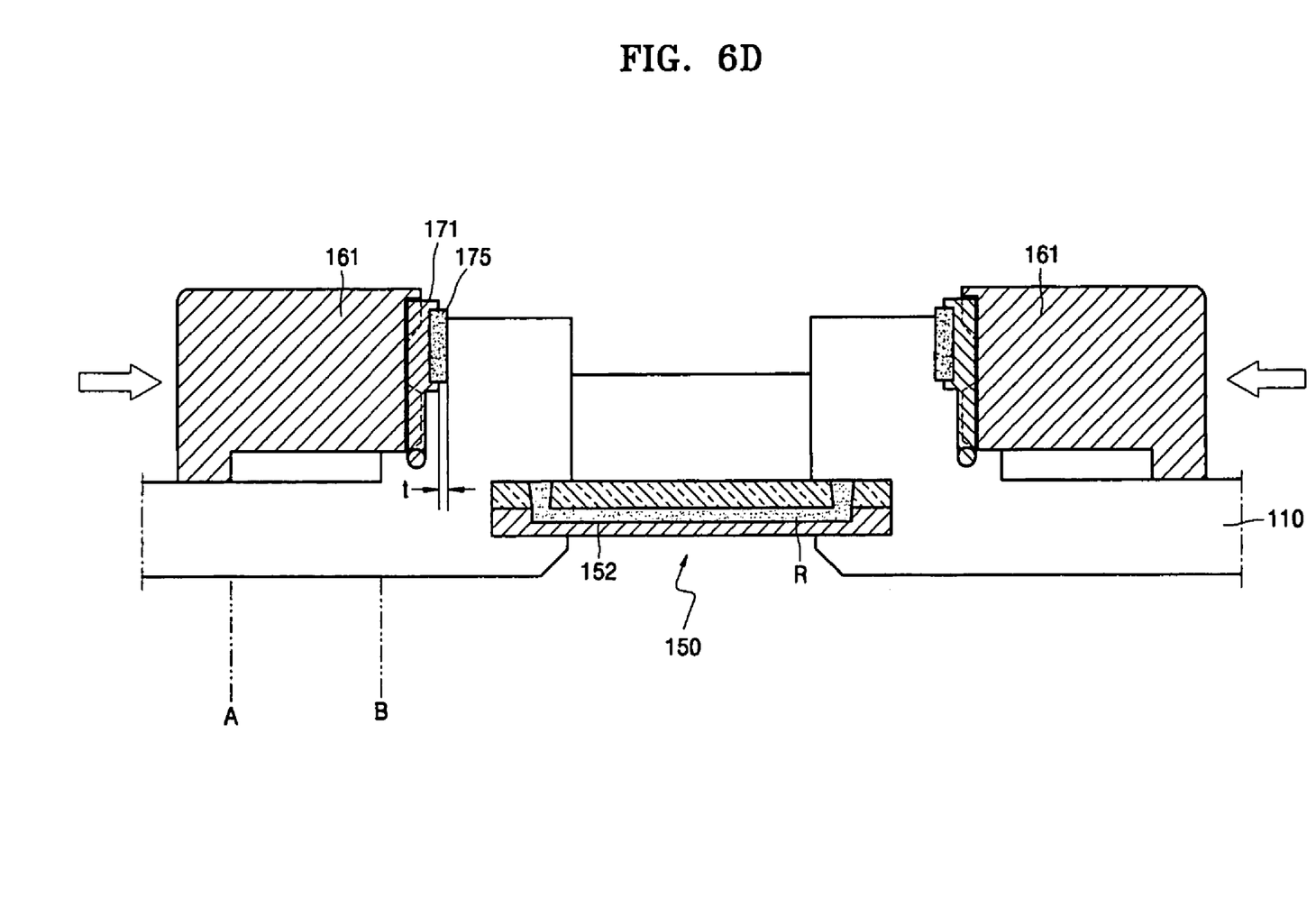
Figure 6E:
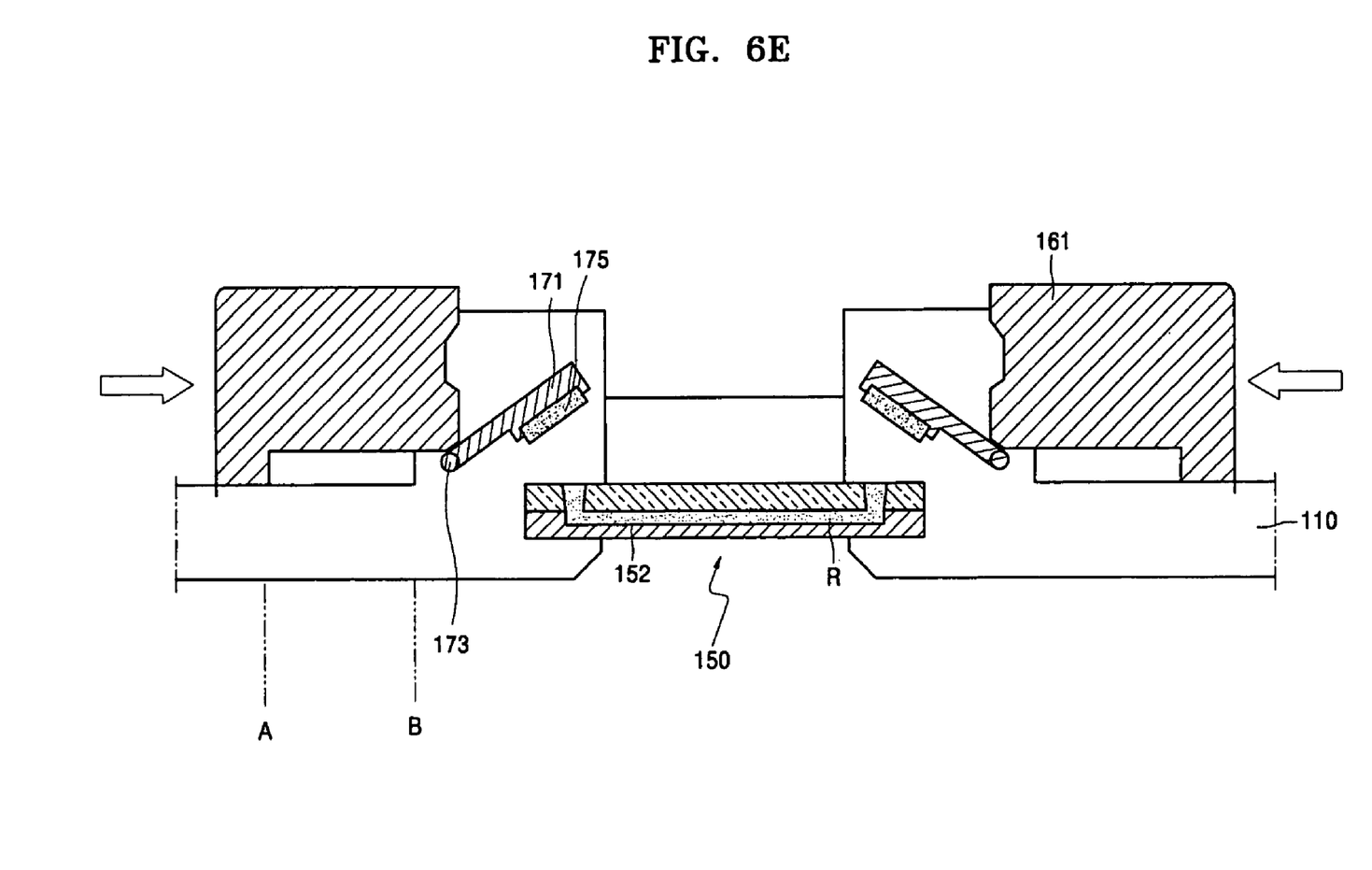
Figure 6F:
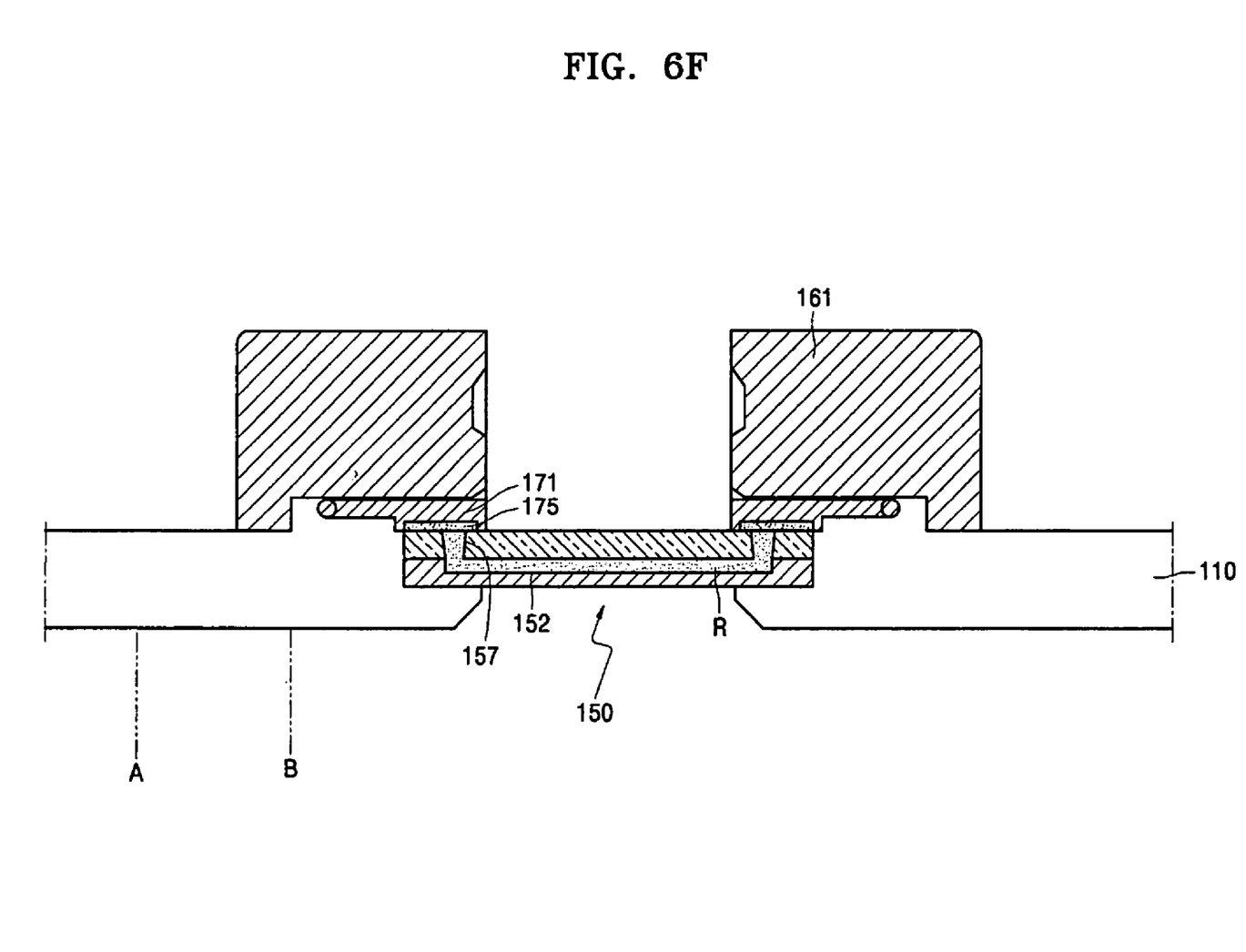

When the injection of the reaction sample R is completed, as shown in FIG. 6C, the cap housing 120 that has been used up is removed and the slider 161 is moved to the inner side. The flipper 171 is supported by being erected inside the slider 161. As shown in FIGS. 6D and 6E, when the slider 161 is pressed from the position A to the position B, the slider 161 pushes the flipper 171 to the inner side so that the flipper 171 pivots around the hinge shaft 173 and flips down toward the microchip 150. As the slider 161 moves to the inner side along the upper surface of the flipper 171 that flips down, the elastic press member 175 formed on the bottom surface of the flipper 171 is compressed in a vertical direction until the step t in the flip-up state is removed. As shown in FIG. 6F, the input hole 157 of the microchip 150 is sealed by the elastic press member 175. The microchip assembly prepared as described above is installed on the thermal cycler that provides a heat circulation reaction. A single or a plurality of microchip assemblies can be installed on the thermal cycler.

When a predetermined thermal cycle is completed, the used microchip assembly is disposed of or undergoes a step of removing the reaction sample remaining inside for recycling. In the latter case, the slider 161 is pushed outside and the flipper 171 is flipped up to be in the erected state. A metal pad can be formed as a flip-up unit (not shown) in a predetermined area on the upper surface of the flipper 171. The flipper 171 can be easily pulled up to the open position by accessing a permanent magnet to the metal pad. When the entrance of the microchip is open, a reaction solution filling the inside of the microchamber is removed and a cleaning step is performed for recycling.

The microchip assembly configured as above according to the present invention has the following merits.

First, the sealing operation of the microchamber can be easily performed. In the microchip assembly of the present invention, since the opening/closing operation of the microchip is performed by means of the flip-up/flip-down mechanism, compared to the other operation mechanism, it is advantageous that less friction is generated during the operation and a relatively smaller operating force is needed. Also, since the microchip assembly has an operational structure which requires relatively less friction, destruction or damage due to friction between parts can be prevented.

Second, since the microchip is fixed and sealed with a relatively simple structure, a manufactured cost is reduced and a disposable microchip assembly can be provided.

Third, the injection hole having a shape matching the injection tool such as a pipette is formed so that the injection tool can be accurately held when the reaction mixture solution is injected. Thus, the leakage of the reaction mixture solution is prevented.

Fourth, since the elastic press member is formed to press and seal the microchip, even when the microchip is heated through a thermal cycle to a predetermined temperature, for example, about 100° C., the microchip can maintain a closed state with respect to steam pressure.

While this invention has been particularly shown and described with reference to preferred embodiments thereof, it will be understood by those skilled in the art that various changes in form and details may be made therein without departing from the spirit and scope of the invention as defined by the appended claims.

What is claimed is:

1. A microchip assembly comprising:
   a base holder;
   a microchip installed on the base holder and having at least one input hole into which a reaction sample is input and at least one microchamber accommodating the input reaction sample;
   a flipper rotatably installed at the outside of the microchip on the base holder and opening and closing the input hole of the microchip while flipping up in a vertically erected state or flipping down in a horizontal state; and
   slider installed at the outside of the flipper on the base holder to be capable of sliding and supporting the flipper in the erected state and flipping down the flipper while moving inside.

2. The microchip assembly as claimed in claim 1, wherein the flipper is arranged in a pair to face each other with respect to the microchip.

3. The microchip assembly as claimed in claim 1, wherein the slider is arranged in a pair at the outside of the flipper.

4. The microchip assembly as claimed in claim 1, wherein an accommodation hole that provides an accommodation space for the microchip is formed in the base holder and a support portion formed along the edge of the accommodation hole to be stepped downward and preventing escape of the microchip.

5. The microchip assembly as claimed in claim 1, wherein a pair of guide members between which the flipper and the slider are inserted and fixed are formed at the outside of the microchip on the base holder.

6. The microchip assembly as claimed in claim 5, wherein a guide piece protruding in a direction is formed on the guide member and a guide groove having a shape matching the shape of the guide piece is formed at the slider.

7. The microchip assembly as claimed in claim 5, wherein a hinge shaft protrudes from both sides of the flipper and a through hole is formed in the guide member into which each hinge shaft is inserted and hinge coupled.

8. The microchip assembly as claimed in claim 1, wherein an elastic press member is formed at a bottom portion of the flipper covering the microchip.

9. The microchip assembly as claimed in claim 8, wherein a cavity is formed at the bottom portion of the flipper and the elastic press member is fixedly inserted in the cavity.

10. The microchip assembly as claimed in claim 8, wherein the elastic press member protrudes from a bottom surface of the flipper to form a step.

11. The microchip assembly as claimed in claim 10, wherein the elastic press member seals the input hole of the microchip in an elastically compressed state so that a bottom surface of the elastic press member forms the same plane with the bottom surface of the flipper.

12. The microchip assembly as claimed in claim 8, wherein the elastic press member is formed of PDMS or silicon rubber as a main material.

13. The microchip assembly as claimed in claim 1, wherein a hook step is formed on a surface of the flipper opposite to the microchip and the flipper is flipped up by a holding unit placed on the hook step.

14. The microchip assembly as claimed in claim 1, wherein a metal pad is formed on a surface of the flipper opposite to the microchip and the flipper pivots into a flip-up state by a permanent magnet which acts a magnetic attraction to the metal pad.

15. The microchip assembly as claimed in claim 1, wherein a cap housing is accommodated on the base holder and at least one injection hole through which the reaction sample is injected toward the microchip thereunder is formed in the cap housing.

16. The microchip assembly as claimed in claim 15, wherein the injection hole has a shape matching the injection tool.

17. The microchip assembly as claimed in claim 15, wherein the injection hole is shaped into a funnel and the injection tool inserted into the injection hole is a pipette.

18. The microchip assembly as claimed in claim 15, wherein a female teeth portion is formed at the injection hole and a male teeth portion matching the female teeth portion is formed at the injection tool that is inserted in the injection hole.

19. The microchip assembly as claimed in claim 15, wherein a lower end surface of the cap housing forms a horizontal surface and contacts the base holder, a protruding press piece protrudes downward than the lower surface of the cap housing from a portion of the cap housing facing the microchip, and the protruding press piece fixedly presses the microchip.

20. The microchip assembly as claimed in claim 15, wherein an indication mark to identify the injection holes formed in multiple numbers is formed on the cap housing.

21. The microchip assembly as claimed in claim 15, wherein the cap housing is formed of an optically transparent material.

* * * * *